United States Patent [19]

Kato et al.

[11] 4,187,014
[45] Feb. 5, 1980

[54] EYE FUNDUS CAMERA

[75] Inventors: Yasuo Kato; Kazuo Nunokawa, both of Tokyo, Japan

[73] Assignee: Tokyo Kogaku Kikai Kabushiki Kaisha, Tokyo, Japan

[21] Appl. No.: 873,719

[22] Filed: Jan. 30, 1978

[30] Foreign Application Priority Data

Jan. 29, 1977 [JP] Japan ................................. 52-8900
Jun. 28, 1977 [JP] Japan ............................... 52-77040

[51] Int. Cl.$^2$ ...................... A61B 3/14; G03B 29/00
[52] U.S. Cl. ........................................ 354/62; 351/7
[58] Field of Search ................... 354/62; 351/6, 7

[56] References Cited

U.S. PATENT DOCUMENTS 3,925,793  12/1975  Matsumura et al. .................. 354/62
4,068,932  1/1978  Ohta et al. ......................... 354/62 X Primary Examiner—John Gonzales
Attorney, Agent, or Firm—Stevens, Davis, Miller & Mosher

[57] ABSTRACT

An eye fundus camera system is provided with a photographic optical system and associated optical axis, an illuminating optical system and associated optical axis and a mark projection system and associated optical axis. The illuminating system is separate from the mark projection system so that operation of the mark projection system during focusing of the photographic optical system will not adversely affect the illumination of an eye fundus.

9 Claims, 10 Drawing Figures

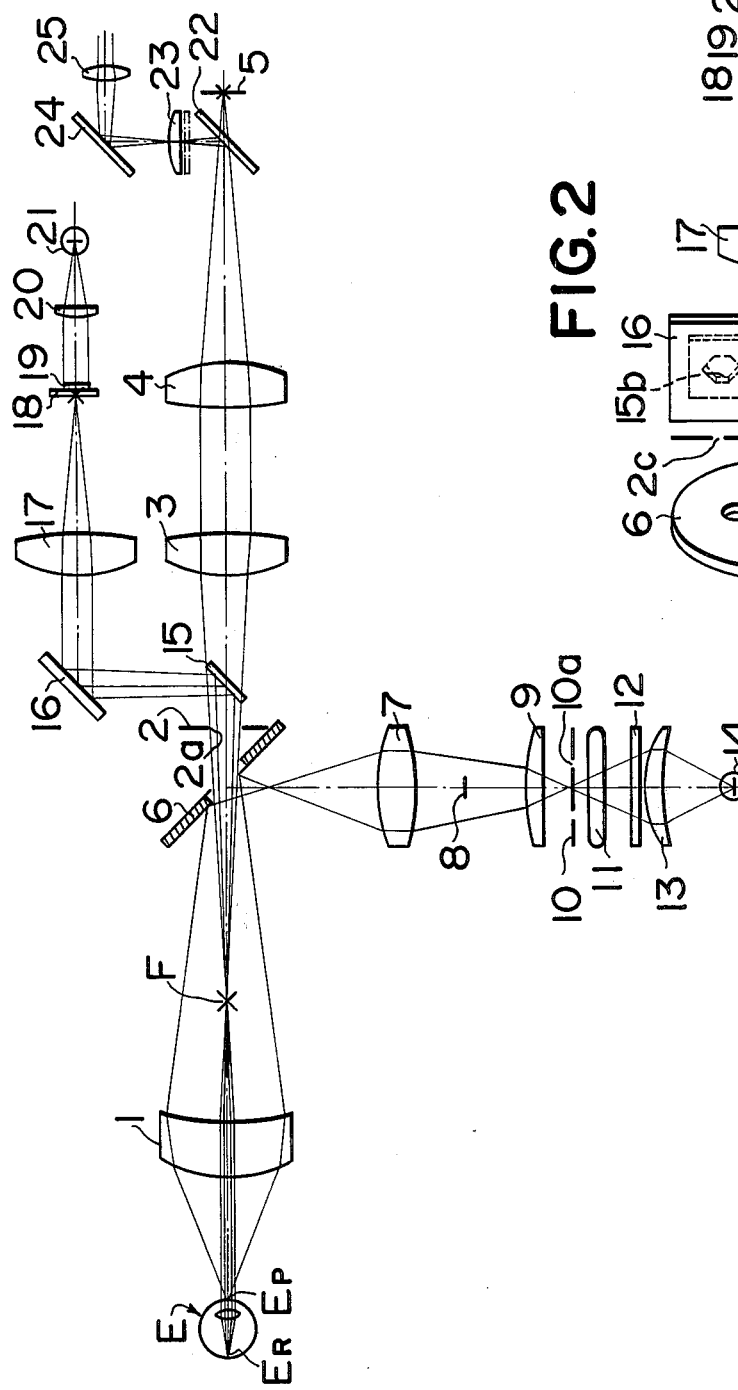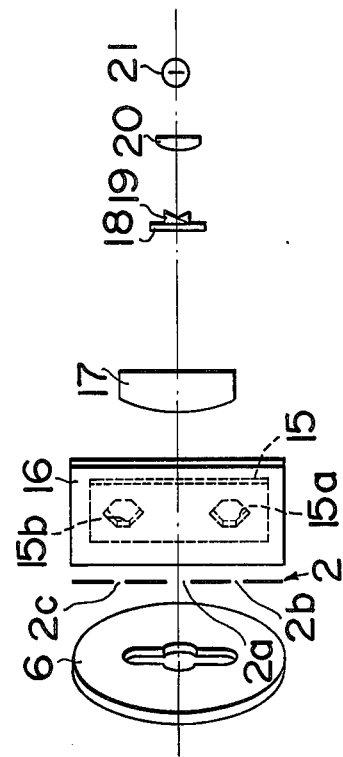

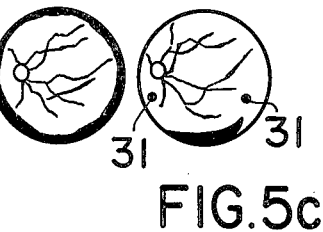
FIG.5c
FIG.6
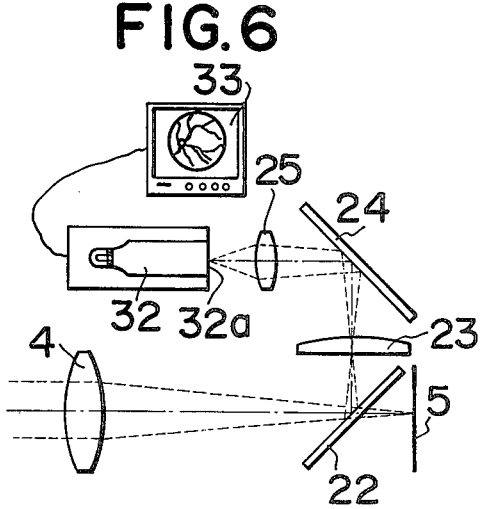

EYE FUNDUS CAMERA

The present invention relates to eye fundus cameras and more particularly to focusing means for eye fundus cameras.

In general, eye fundus cameras include a fundus illuminating system, a photographing optical system and a finder system for determining visual field and for focusing. Conventional eye fundus cameras are generally provided with a transparent plate having cross lines printed thereon so that focusing is performed by bringing an image produced by the photographing optical system to a position aligned with the cross lines on the transparent plate. In this known arrangement, it is quite troublesome to accomplish a precise focusing because there may be a change in the visibility of the observer during the focusing operation.

In order to eliminate the above problem, it has already been proposed to provide in the illuminating system a mark projecting device which generally includes deflecting prism means so that the focusing can be determined by the alignment condition of the projected mark. The arrangement has been found to be convenient as far as focusing is concerned, however, it requires a complicated mechanism which may include cams or the like for interconnecting the photographing optical system and the mark projecting system for maintaining the necessary conjugate relationship therebetween. Further, when the mark projecting system is so arranged that the mark projection is performed through a relay lens in the illuminating system, there may be a further problem because the intensity of illumination may be changed by the focusing operation.

Another problem in eye fundus cameras has been found in prevention of corneal reflection from entering the photographing system. Conventional eye fundus cameras are so designed that the corneal reflection is prevented from entering the photographing optical system as long as the eye to be inspected is correctly positioned with respect to the camera in respect of the alignment of the visual axis of the eye and the optical axis of the camera as well as the distance between the eye and the camera. However, in conventional eye fundus cameras, there has been no means for confirming the correct positioning of the eye.

It is therefore an object of the present invention to provide eye fundus cameras including focusing means which is simple in construction and easy to operate.

Another object of the present invention is to provide eye fundus cameras including a mark projecting system for focusing, which can be interconnected with the photographing optical system by a simple mechanism.

A further object of the present invention is to provide eye fundus cameras having focusing means which is easy to operate but does not have any influence on the illuminating system.

Still further object of the present invention is to provide eye fundus cameras including means for confirming the correct positioning of the eye to be inspected with respect to the camera.

According to the present invention, the above and other objects can be accomplished by an eye fundus camera comprising a photographing optical system which includes at least an objective lens having an optical axis, an imaging lens and axially movable focusing means for adjusting the photographing optical system to obtain a desired focus condition; eye fundus illuminating system including illuminating light source means and an apertured reflecting means disposed in the optical axis of the objective lens in the photographing optical system for directing illuminating light from the light source means to the objective lens so that the illuminating light is projected through the objective lens; and a mark projecting system including light splitting means provided behind the reflecting means adjacent to a position conjugate with an eye to be inspected with respect the objective lens, mark projecting means for projecting a focusing mark through the light splitting means and the objective lens to the eye to be inspected, and means for interconnecting the mark projecting means with the focusing means so that focusing of the photographing optical system can be judged by the mark projected on the eye.

According to the present invention, the mark projecting system is not provided in the illuminating system but in a separate optical path which is divided out from the photographing optical path so that there is no possibility that the illuminating condition is adversely affected by the focusing operation. Further, it is possible to interconnect the mark projecting system with the focusing means of the photographing optical system by means of a very simple mechanism. For example, the mark projecting system may include a reflecting surface for directing the light path in parallel with the optical path in the photographing optical system and the mark may be positioned in conjugate with the photographing film plane. In such an arrangement, the mark projecting system may include a relay lens which may simply be moved as a unit with the mark and the focusing means of the photographing optical system.

It has been found that the present invention is particularly useful in an eye fundus camera in which focusing operation is performed by projecting the mark with an infrared ray. As well known in the art, the focusing operation under an infrared ray is performed by video means which receives the infrared ray reflected at the eye fundus and converts it into a visual image on a video tube. In this type of eye fundus camera, it is very difficult to judge the focus condition because the visibility and contrast of the image on the video tube are extremely poor. According to the present invention, the focus condition can be readily judged by the image of the projected mark.

Preferably, the mark projecting system includes deflecting prism means and the mark is in the form of a slit, the deflecting prism means being so constructed that the projected image of the mark assumes the same configuration as the slit when the photographing optical system is in focused condition. For the purpose, this deflecting prism means may include a pair of deflecting prisms for dividing light through the mark into two parts and deflecting the divided lights in opposite directions.

In order to ascertain the correct positioning of the eye to be inspected with respect to the objective lens, second mark means such as spot light means may be positioned at a position conjugate with the eye with respect to the objective lens whereby the location and the focusing condition of the second mark means can be used as a measure for the position of the eye.

The above and other objects and features of the present invention will become apparent from the following descriptions of a preferred embodiment taking reference to the accompanying drawings, in which:

FIG. 1 is a diagrammatical side view of the optical arrangement of an eye fundus camera in accordance with one embodiment of the present invention;

FIG. 2 is a fragmentary plan view particularly showing the focusing mark projecting system;

Figure 3A:
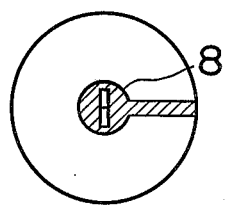
Figure 3B:
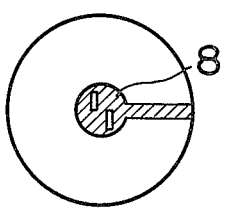
Figure 3C:
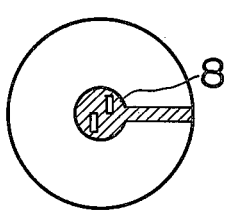
Figure 4:
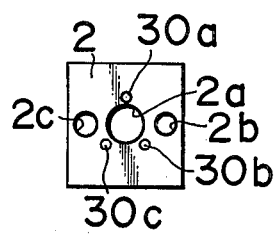

FIGS. 3 (a), (b) and (c) show projected images of the focusing mark;

FIG. 4 is a front view showing position indicating marks provided on the aperture plate;

FIGS. 5 (a), (b) and (c) show images of the positioning marks; and

FIG. 6 is a fragmentary view showing a finder system for use with an infrared ray.

Referring now to the drawings, particularly to FIG. 1, the eye fundus camera shown therein includes a photographing optical system which comprises an objective lens 1 adapted to be positioned against an eye E to be inspected, an aperture plate 2 having an aperture 2a adapted to be positioned in conjugate with the pupil Ep of the patient's eye E with respect to the objective lens 1, a focusing lens 3, an imaging lens 4 and a photographing film 5, the lenses 3 and 4 defining an aforcal optical system. In front of the film 5, there is provided a reflecting mirror 22 defining a reflecting path on which a field lens 23 is located. As well known in the art, the mirror 22 is retractable as shown by phantom lines in FIG. 1 during photography. The light path through the field lens 23 is reflected by a mirror 24 and an eye-lens 25 is provided to define a finder system.

The eye fundus camera further includes an illuminating optical system which comprises an apertured mirror 6 provided in the optical path of the photographing optical system to define a illuminating optical path. In the illuminating optical path, there is provided a relay lens 7, a condenser lens 9, an annular slit plate 10 having an annular slit 10a therein, a flash lamp 11 for photographing, a heat insulating filter 12, a condenser lens 13 and an illuminating light source 14 such as a tungsten lamp. The lamp 11 is energized when the shutter (not shown) in front of the film 5 is released and the mirror 22 is retracted. The light from the light source 11 or 14 is passed through the annular slit 10a in the plate 10 and focused in an annular form on the apertured mirror 6 to be reflected thereby. The light reflected by the mirror 6 is projected through the objective lens 1 to illuminate the fundus $E_R$ of the patient's eye E.

In order to facilitate focusing of the photographing optical system, there is further provided a mark projecting system which includes a reflecting mirror device 15 provided behind the apertured plate 2 in the optical path of the photographing optical system, a reflecting mirror 16, a relay lens 17, a mark 18 in the form of an elongated slit, a deflecting prism assembly 19 attached to the mark 18, a condenser lens 20 and a light source 21, so that the light from the source 21 is passed through the condenser lens 20 to illuminate the slit mark 18 to project the mark 18 on the patient's eye E.

The deflecting prism assembly 19 includes a pair of prism elements for dividing the light through the slit mark into two parts and deflecting the divided light parts in two different directions. More specifically, the light portions passing through the upper and lower halves of the slit mark are deflected in the opposite directions with respect to the optical axis of the mark projecting system. The light which has passed through the slit mark is directed through the relay lens 17, the mirrors 16 and 15, the aperture plate 2 and the aperture in the mirror 6 to be focused at a position F which is conjugate with the film 5 with respect to the lenses 3 and 4. The mark projecting light is then projected through the objective lens 1 to the patient's eye E.

The mark projecting light is focused at the fundus $E_R$ of the eye E to produce an image which is identical in configuration to that of the slit mark 18 as shown in FIG. 3(a) when the photographing optical system is in the focused position. However, when the photographing optical system is out of focus, there is produced a split image as shown in FIGS. 3(b) or (c).

In order to reflect the light portions split by the prism assembly 19 toward the objective lens 1, the reflecting mirror device 15 includes a pair of reflecting surfaces 15a and 15b which are disposed symmetrically with respect to the optical axis of the photographing system. The construction of the mirror device 15 does not provide any obstruction to the light which has been reflected at the eye fundus $E_R$ and passing along the optical path of the photographing system to be projected to the film 5. The aperture plate 2 has a pair of apertures 2b and 2c which are located at the opposite sides of the central aperture 2a for passing the light portions reflected by the surfaces 15a and 15b. Further, the mirror 6 has an aperture which is so shaped that the light portions from the mirror surfaces 15a and 15b passed therethrough without any difficulty.

In order to obtain a higher contrast of the projected slit mark image, it is desirable to interrupt the background illumination at an area where the slit mark is projected. For the purpose, the illustrated eye fundus camera includes an interrupting plate or shutter 8 which is retractably positioned in the illuminating system at a position conjugate with the eye fundus $E_R$. The plate 8 of course has an area which can adequately cover the projected mark image.

In the optical system shown in FIGS. 1 and 2, the focusing lens 3 is axially moved as a unit with the relay lens 17, the mark 18, the prism assembly 19, the condenser lens 20 and the light source 21 for focusing operation. Where the photographing optical system is so constructed that the lens 3 is omitted and focusing is performed by moving the imaging lens 4 with the film 5, the aforementioned elements in the mark projecting system may be axially moved as a unit with the lens 4 and the film 5.

Referring now to FIG. 4, the aperture plate 2 has on its front surface three spot light sources 30a, 30b and 30c which are positioned symmetrically with respect to the center of the aperture 2a. Since the light sources 30a, 30b and 30c are located outside the apertures 2a, 2b and 2c, they do not interfere with any of the optical paths. The light sources 30a, 30b and 30c may comprise light emitting diodes (LED) and the light from the diodes is projected through the objective lens 1 to the cornea $E_P$ of the patient's eye E. The light reflected at the eye corneas $E_C$ is passed through the photographing optical system to be observed through the finder system.

In the optical system shown in FIG. 1, the aperture plate 2 is located in conjugate with the surface of the eye cornea $E_P$ with respect to the objective lens 1 and the mirror 6 is located in the vicinity of the conjugate position. Therefore, as long as the patient's eye is located in a correct position or, in other words, when the eye E is located in a position where the visual axis of the eye E is aligned with the axis of the objective lens 1 and the surface of the cornea $E_P$ is at a correct distance from the objective lens 1, the light from the source 11 or 14 is passed through the annular slit 10a in the plate 10 to be focused in an annular configuration on the apertured mirror 6 and then reflected by the mirror 6 and passed through the lens 1 to be projected on the corneal surface to produce an annular image of the light source. The illuminating light is then in part reflected at the surface of the cornea $E_P$ and the remainder is passed into the patient's eye to illuminate the eye fundus $E_R$. Since the illuminating light is thus focused in an annular configuration on the eye cornea $E_P$, even the innermost part of the light which has been reflected by the cornea $E_P$ is prevented by the mirror 6 from entering the photographing optical path. The light sources 30a, 30b and 30c are effective in judging the position of the patient's eye E with respect to the objective lens 1.

Figures 5A, 5B:
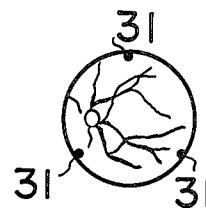

As previously described, the light sources 30a, 30b and 30c are located in conjugate with the cornea $E_P$ of the patient's eye E with respect to the objective lens 1. Therefore, as long as the corneal surface is correctly positioned with respect to the objective lens 1, the lights from the spot light sources are reflected at the corneal surface and the reflected lights are passed through the photographing optical system to be focused in the finder system. By properly determining the positions of the spot light sources 30a, 30b and 30c on the aperture plate 2, it is possible to have the images of the light sources focused at the positions as shown by 31 in FIG. 5(a). In such an arrangement, when the patient's eye E is not positioned at the correct distance from the objective lens 1, the images of the light sources will become as shown in FIG. 5(b) while the images will be displaced as shown by 31 in FIG. 5(c) when the visual axis of the eye E is not aligned with the optical axis of the lens 1.

The present invention can well be applied to an eye fundus camera wherein the focusing is performed using an infrared ray. For this purpose, the illuminating system may include a filter which is transparent only to the infrared ray. Such filter may be positioned between the light sources 11 and 14 in FIG. 1 so that the infrared ray be used only for focusing and visual observation. Similarly, the mark projection system may be provided with a filter which is transparent only to an infrared ray.

FIG. 6 shows a finder system using such infrared ray. The light which has been reflected by the mirror 22 and passed through the field lens 23 is reflected by the mirror 24 and passed through the relay lens 25 to be projected on the imaging surface 32a of a converter tube 32. A visible image is then produced on a video device 33.

The invention has thus been shown and described with reference to specific embodiments, however, it should be noted that the invention is in no way limited to the details of the illustrated arrangements but changes and modifications may be made without departing from the scope of the appended claims.

We claim:

1. An eye fundus camera comprising a photographic optical system which includes at least an objective lens having an optical axis, an imaging lens and axially movable focusing means for adjusting the photographic optical system to obtain a desired focus condition; an eye fundus illuminating system including illuminating light source means directing light along an illuminating optical axis and an apertured reflecting means disposed in the optical axis of the objective lens in the photographic optical system for directing illuminating light from the illuminating optical axis to the objective lens so that the illuminating light is projected through the objective lens; and a focusing mark projecting system having an optical axis and which is separate from said illuminating optical axis including light splitting means provided behind the reflecting means adjacent to a position conjugate with an eye to be inspected with respect to the objective lens, mark projecting means for projecting a focusing mark along the optical axis of said mark projecting system through the light splitting means and the objective lens to the eye to be inspected, and means for interconnecting the mark projecting means with the focusing means so that focusing of the photographic optical system can be judged by the mark projected on the eye.

2. An eye fundus camera in accordance with claim 1 in which said focusing mark projecting system includes deflecting prism means and the mark is in the form of a slit, the deflecting prism means being so constructed that the projected image of the mark assumes the same configuration as the slit when the photographing optical system is in a focused condition.

3. An eye fundus camera in accordance with claim 2 in which said deflecting prism means includes a pair of deflecting prisms for dividing light passing through the mark into two parts and deflecting the two light parts in opposite directions.

4. An eye fundus camera in accordance with claim 1 in which said focusing mark projecting system optical axis is in parallel with the optical axis of the photographic optical system, said mark projection means including a mirror means for directing light from the optical axis of the focusing mark projecting system toward said light splitting means, said focusing mark being located along said optical axis of the mark projecting system in a position in conjugate with the imaging plane in the photographic optical system.

5. An eye fundus camera in accordance with claim 4 in which said focusing mark projecting system includes a pair of deflecting prisms for dividing light passing through the mark into two parts and deflecting the two light parts in opposite directions with respect to the optical axis of the focusing mark projecting system, said light splitting means including a pair of reflecting surfaces which are positioned symmetrically with respect to the optical axis of the photographic optical system and deviated from the optical axis in the direction of the deflection of the prisms.

6. An eye fundus camera in accordance with claim 1 in which said illuminating system includes a retractable shutter for interrupting illumination of an area where the mark is projected.

7. An eye fundus camera in accordance with claim 1 in which said focusing mark projecting means includes infrared light source means for projecting the mark by an infrared ray.

8. An eye fundus camera in accordance with claim 1 which further includes mark means adapted to be located at a portion substantially conjugate with cornea of patient's eye with respect to the objective lens.

9. An eye fundus camera in accordance with claim 8 in which said mark means is a spot light source means.

* * * * *